United States Patent [19]

Latimer et al.

[11] Patent Number: 5,760,307
[45] Date of Patent: Jun. 2, 1998

[54] EMAT PROBE AND TECHNIQUE FOR WELD INSPECTION

[76] Inventors: Paul J. Latimer, 303 Juniper Dr.; Daniel T. MacLauchlan, 517 Little Creek Rd., both of Lynchburg, Va. 24502

[21] Appl. No.: 531,573

[22] Filed: Sep. 7, 1995

Related U.S. Application Data

[63] Continuation-in-part of Ser. No. 210,848, Mar. 18, 1994, abandoned.

[51] Int. Cl.$^6$ ................................................. G01N 29/10
[52] U.S. Cl. .................... 73/643; 73/598; 73/600; 73/620; 73/624; 73/627
[58] Field of Search .................... 73/643, 598, 600, 73/602, 620, 622, 624, 627, 629, 634, 621; 208/104; 364/507

[56] References Cited

U.S. PATENT DOCUMENTS

| | | | |
|---|---|---|---|
| 3,918,295 | 11/1975 | Herbertz | 73/643 |
| 4,289,030 | 9/1981 | Alers et al. | 73/643 |
| 4,481,824 | 11/1984 | Fujimoto et al. | 73/643 |
| 4,593,568 | 6/1986 | Telford et al. | 73/629 |
| 5,060,518 | 10/1991 | Aleshin et al. | 73/627 |
| 5,085,082 | 2/1992 | Cantor et al. | 73/643 |
| 5,154,081 | 10/1992 | Thompson et al. | 73/643 |
| 5,237,874 | 8/1992 | Latimer et al. | 73/643 |
| 5,359,898 | 11/1994 | Latimer | 73/634 |
| 5,497,662 | 3/1996 | Dykes | 73/634 |
| 5,537,876 | 7/1996 | Davidson et al. | 73/643 |

Primary Examiner—Hezron E. Williams
Assistant Examiner—Nashmiya Fayyaz
Attorney, Agent, or Firm—Daniel S. Kalka; Robert J. Edwards

[57] ABSTRACT

A method and apparatus of inspecting for flaws in a specular reflector, where the flaws having an expected length and the reflector is electrically conductive. The method includes directing a beam of an electromagnetic acoustic transmitting transducer along a beam axis toward the specular reflector for producing a reflected electromagnetic acoustic beam. The transmitted beam has side lobes with zero points therebetween, at least some of the side lobes being major side lobes. The reflected beam is received using an electromagnetic acoustic receiving transmitter set at an angle to the beam axis, the angle being selected to be at one of the zero points and past all of the major lobes of the transmitted beam to eliminate root and crown signals of the weld, in the reflected signal.

8 Claims, 6 Drawing Sheets

10, 16

EMAT PROBE AND TECHNIQUE FOR WELD INSPECTION

This is a Continuation-In-Part of application Ser. No. 08/210,848 filed Mar. 18, 1994 now abandoned.

BACKGROUND OF THE INVENTION

1. FIELD OF THE INVENTION

The present invention relates, in general, to EMAT inspections of welds, and in particular, to a new and useful method and apparatus for using crossed or collinear EMATs, to eliminate root and crown signals, while still generating defect or flaw signals for the inspection of a weld or other structure.

2. DESCRIPTION OF THE RELATED ART

The examination of welds by conventional ultrasonic sensors typically involves a raster type scan in which the time between the resulting crown and root signals is examined for the presence of flaws. This is a slow process that is not well suited for automation because of the requirements for a fluid couplant and a complex mechanical scanner to perform the raster scan.

Electromagnetic Acoustic Transducers (EMATS) are a non-contact method of producing ultrasonic waves in conductors. An EMAT in its simplest form is a coil of wire and a magnet. The RF signals applied to the EMAT coil induce eddy currents at the surface of the conductor. The surface currents interact with the magnetic field, producing the Lorentz force in a manner similar to an electric motor. The disturbance is transferred to the lattice of the solid, and this is the source of the acoustic wave. The process is reciprocal. If an acoustic wave strikes the surface of a conductor in the presence of a magnetic field, induced currents are generated in the receiving coil much as an electric generator. For the case of ferromagnetic conductors the process is more complicated. In addition to the Lorentz force there are additional stresses produced by magnetostriction. In many cases, the magnetostrictive stresses enhance the signal to much higher levels than could be obtained by the Lorentz interaction alone.

The advantages of EMATs result from the fact that they require no ultrasonic couplant and they are capable of producing more wave modes than conventional piezoelectric ultrasonic techniques. The fact that no couplant is required allows EMATs to scan at very high speeds. Also, the absence of couplant and the use of electromagnets allow EMATs to operate at high temperatures. EMATs are capable of producing all of the modes that are produced by conventional ultrasonics and one mode that is unique to EMATs— the angle beam, horizontally polarized (SH) shear waves. This mode when produced by conventional ultrasonic techniques requires either epoxy or a highly viscous couplant and, thus, it cannot be used for scanning. The SH shear waves are useful because they undergo no mode conversion upon reflection from an interface. This is particularly useful for inspections of welds and components with complex geometry. SH shear wave EMATs have one more advantage; the beam angle can be changed from 0° to 90° by changing the frequency. Surface waves are efficiently produced by EMATs without the wedge noise and damping of the surface waves by couplant that is typical of conventional ultrasonics. Surface waves are very efficiently produced in nonferromagnetic materials such as aluminum using the normal field of a permanent magnet. This is a very compact and useful EMAT sensor for scanning the various aluminum alloys.

EMATs or Electromagnetic Acoustic Transducers, are ideally suited for an automated environment. They do not require a fluid couplant and, therefore, very rapid automated scans can be performed. EMATs are also useful for weld inspection. A weld has a crown, which is the top of the weld, and it consists of a section of weld metal that extends above the surfaces of the parts being joined. The weld also has a root, which is the bottom part of the weld, and it consists of a layer of weld metal that extends below surfaces of the parts being joined. It is convenient, in many cases, to leave the crown and root in the as-welded condition because of the time and expense required to grind the root and crown flush with the joined parts. In a conventional ultrasonic inspection, the root and crown produce signal by specular reflection that is difficult to distinguish from flaw signals. The specular reflector acts as a mirror in optics—the angle of incidence (angles measured with respect to a normal to the reflector) is equal to the angle of reflection. A specular reflector does not alter the curvature of the wave fronts, as in diffraction, but merely redirects the rays (the rays are lines perpendicular to the wavefronts) at the angle of reflection. In contrast, when diffraction takes place, as when an ultrasonic wave strikes a small defect within the weld, the curvature of the wavefronts is changed. The rays are then spread over increasing angles as the wavelength of the ultrasound approaches the dimensions of the defect or discontinuity in the weld. This allows the discontinuity to be detected over a wide range of angles as compared to the narrow angular detection range with specular reflection. It is desirable to flood the weld region with sound and thus eliminate the raster scan (motion toward and away from the weld). The presence of the root and crown signals, however, complicate data interpretation. It is desirable to eliminate the root and crown signals, however, there are no known methods in the prior art for achieving this objective. The present disclosure describes unique methods for flaw detection in welds using EMATs that eliminate the root and crown signal. In addition, both techniques allow flaws to be detected in the weld regardless of the flaw orientation. Therefore, by merely performing a linear scan of the weld, all flaw orientations can be detected without the presence of a root and crown signal.

SUMMARY OF THE INVENTION

Experiments have demonstrated that a crossed beam EMAT can be used to eliminate the root and crown signals and yet allow defect signals to be detected. The root and crown act as specular reflectors and, therefore, the angle of incidence is equal to the angle of reflection. A small flaw, however, acts as a point source with reflected radiation diffracted over a wide angle. Thus, it was possible to rotate the transmitting and receiving EMATs to detect the defect signal but not the specular reflected signals from the root and crown. Laboratory results have demonstrated the feasibility of detecting both EDM (electrical discharge machining) notches and induced flaws in a 2219 aluminum weld. Three defects were identified using the technique. These three flaws were then examined with real time radiography and, identified as porosity, an "L" shaped crack on the center line of the weld, and a region where there was lack of fusion.

It has been observed in practice that large natural flaws can be detected using the diffraction technique. This is possible because most natural flaws have many small facets and branches that act as point sources for diffraction. Therefore, most large natural flaws act like a series of connected diffraction centers. Thus, as an example, cases of nonfusion several inches in length have been detected. Also, long cracks have similarly been detected.

As a variation of the crossed beam EMAT of the invention, it was observed that two pitch-catch collinear, (focused or nonfocused) sensors could be rotated with respect to the weld center line to achieve the same results as described above for the crossed beam sensor. Although, the probe in this case may not be unique, the technique is unique. This technique is actually more useful in practice than the crossed beam EMAT because the focused sensors increase the signal to noise ratio. Also, the angle between the sensor and the normal to the weld (the diffraction angle) can be conveniently adjusted with this technique. This technique has been used to check many aluminum and steel welds using surface waves to replace penetrant examination and magnetic particle examination for surface breaking flaws in welds. It has also been used extensively with shear waves for a volumetric inspection of many different welds to replace radiography. The technique has been used to detect every weld defect that can be detected by conventional methods. It has also been used to detect very tight fatigue crack that are difficult to detect by some of the other standard tests such as penetrant examination.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

The principle of operating a crossed beam sensor is based on the fact that the root and crown act as a specular reflector (for reasonably smooth welds), and, therefore, the angle of incidence is equal to the angle of reflection. A small flaw, however, acts as a point source and the diffracted radiation is scattered over a wide angle. Also, a large natural flaw acts as a series of point sources with a large diffracted radiation pattern. Thus, it is possible to rotate the transmitting and receiving EMATs to detect the defect signal but not the specularly reflected signals from the root and crown. In practice, the transmitter is positioned perpendicular to the flaw. The receiver is rotated relative to the transmitter at an angle which is past all of the major side lobes and at one of the zero points. This position is then the operating angle for the combination sensor.

Figure 1:
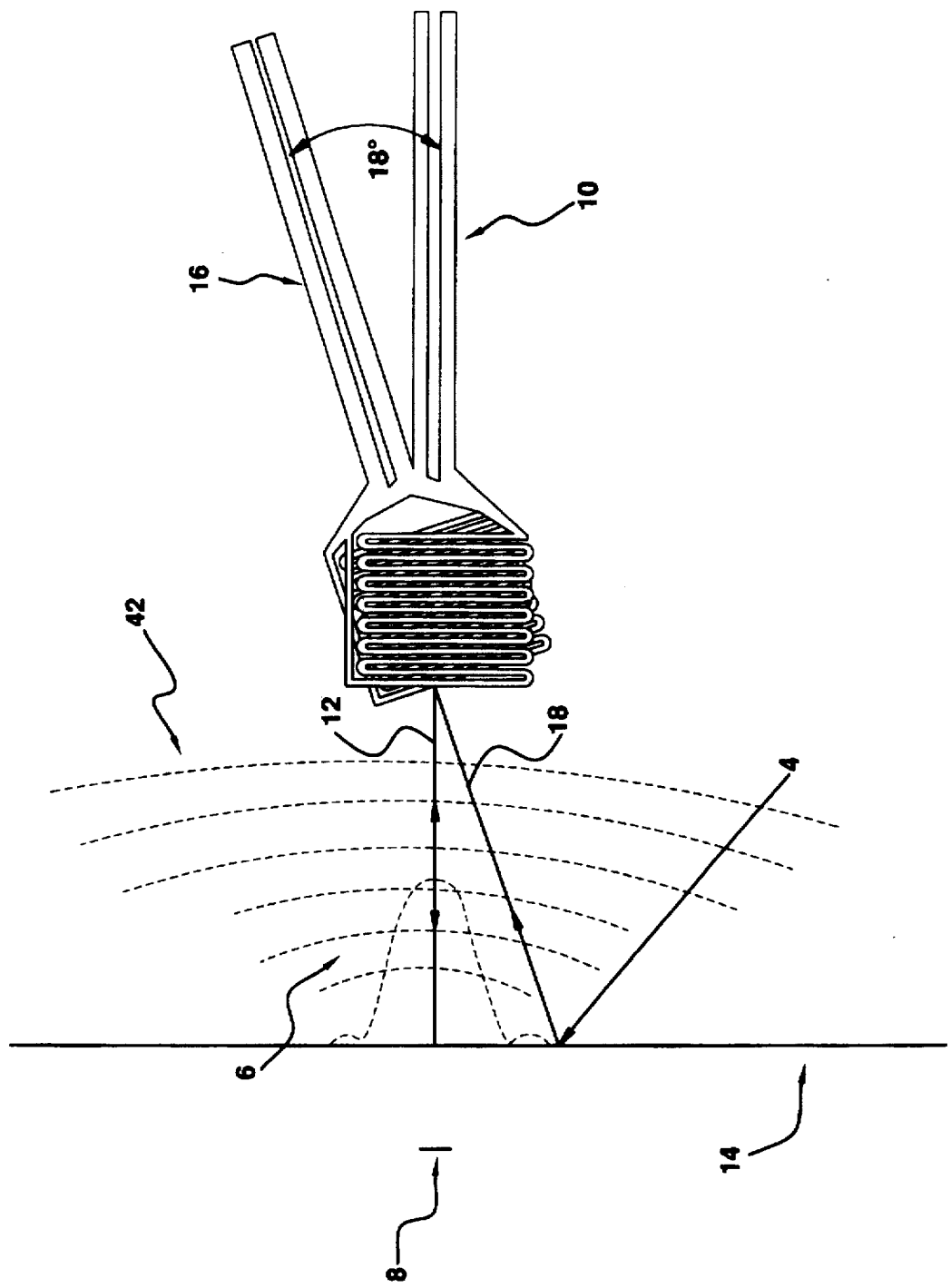
FIG. 1 is a schematic drawing showing the set-up of a crossed beam EMAT weld sensor in accordance with the present invention.

As shown in FIG. 1, an EMAT transmitter 10, excited by a pulsed RF signal, of conventional construction, is oriented to direct its transmission beam 12 perpendicular to the flat surface of a specular reflector 14 which may include a weld crown or root, in particular, a surface containing a weld to be inspected according to the present invention. A receiving EMAT 16 is oriented at an angle which is selected according to the present invention and is advantageously 18° in FIG. 1, to the beam axis of the transmitter 10, for receiving reflected acoustic beams 18 and also reflected beams parallel to the transmission beam 12. The diffracted wavefronts 42 from the defect 8 are detected by the receiver EMAT 16. FIG. 1 shows the specular reflection pattern 6 and the zero point 4 from the specular refection 6 not detected by receiver EMAT 16. The beam from the zero point 4 of the specular reflection 6 is not received by the receiver EMAT.

According to the present invention, the angle between the transmitter and receiver is selected so that the receiver is past all major side lobes of the transmission beam and at one of the zero points.

Figure 2:
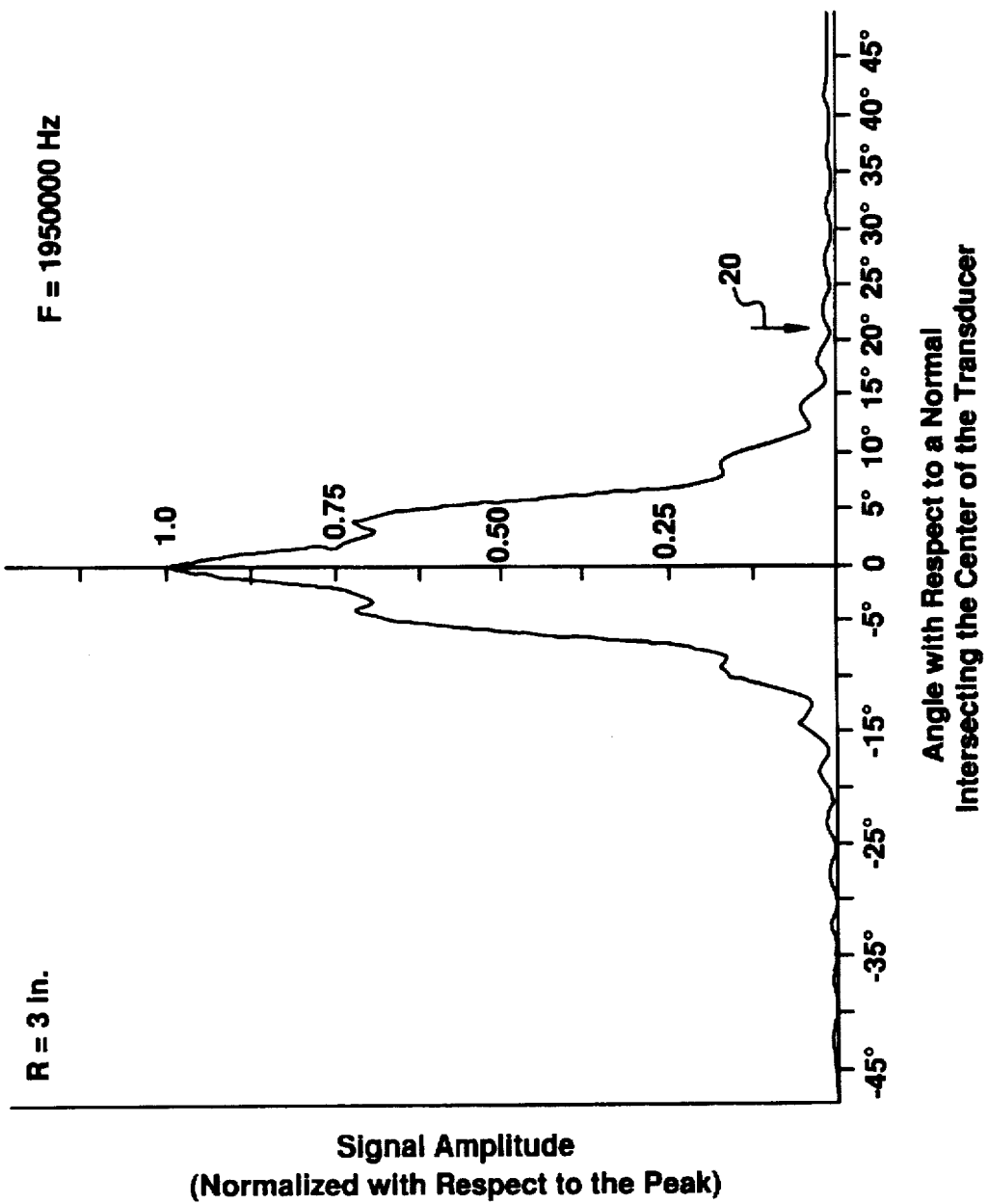
FIG. 2 is a theoretical plot of a beam profile which agreed with observations made in the laboratory, showing the lobes of the beam.

In order to compare the experimental observations with some theoretical results, a computer program using Huygen's principle was used to plot a theoretical directivity curve (also called a diffraction curve) of the transmitter EMAT at a metal path of three inches. The directivity curve expresses the directional characteristics of the transmitted sound field (Krautkramer and Krautkramer, Ultrasonic Testing of Materials, Second Edition, Springer Verlag, New York, 1977.) The metal path refers to the distance along which the sound actually propagates in the metal. The theoretical curve is actually the diffraction pattern observed when plane waves propagate through a rectangular aperture of the same dimension as a transmitter EMAT. Huygen's principle was used to plot the curve because Huygen's principle is valid for all points in front of the EMAT transmitter. In practice, this curve provides the directional characteristics of the transmitter. The signal amplitude from the rectangular transmitter (or emitter) at a metal path of three inches was normalized with respect to the peak amplitude and plotted on the vertical axis. The horizontal axis represented the angle with respect to a normal intersecting the center line of the transmitter. The results shown in FIG. 2 agree with observations made in the laboratory (the positions of the predicted zeroes agreed with the experimentally observed position of the zeroes). There were basically two major side lobes that were passed as the receiver was rotated to a zero point of the EMAT transmitter and thus there was no detectable signal. This corresponds to the arrow 20, marking a zero point on the plot between the minor side lobes. The receiver EMAT should be rotated past all major side lobes to a zero point and left at that angle as long as the distance from the EMAT sensor to the weld center line is held constant.

In practice, the sensors (transmitter and receiver EMATS) could be SV EMATs (vertically polarized shear wave EMATS), SH EMATs (horizontally polarized EMATs), or surface wave EMATs.

Figure 3:
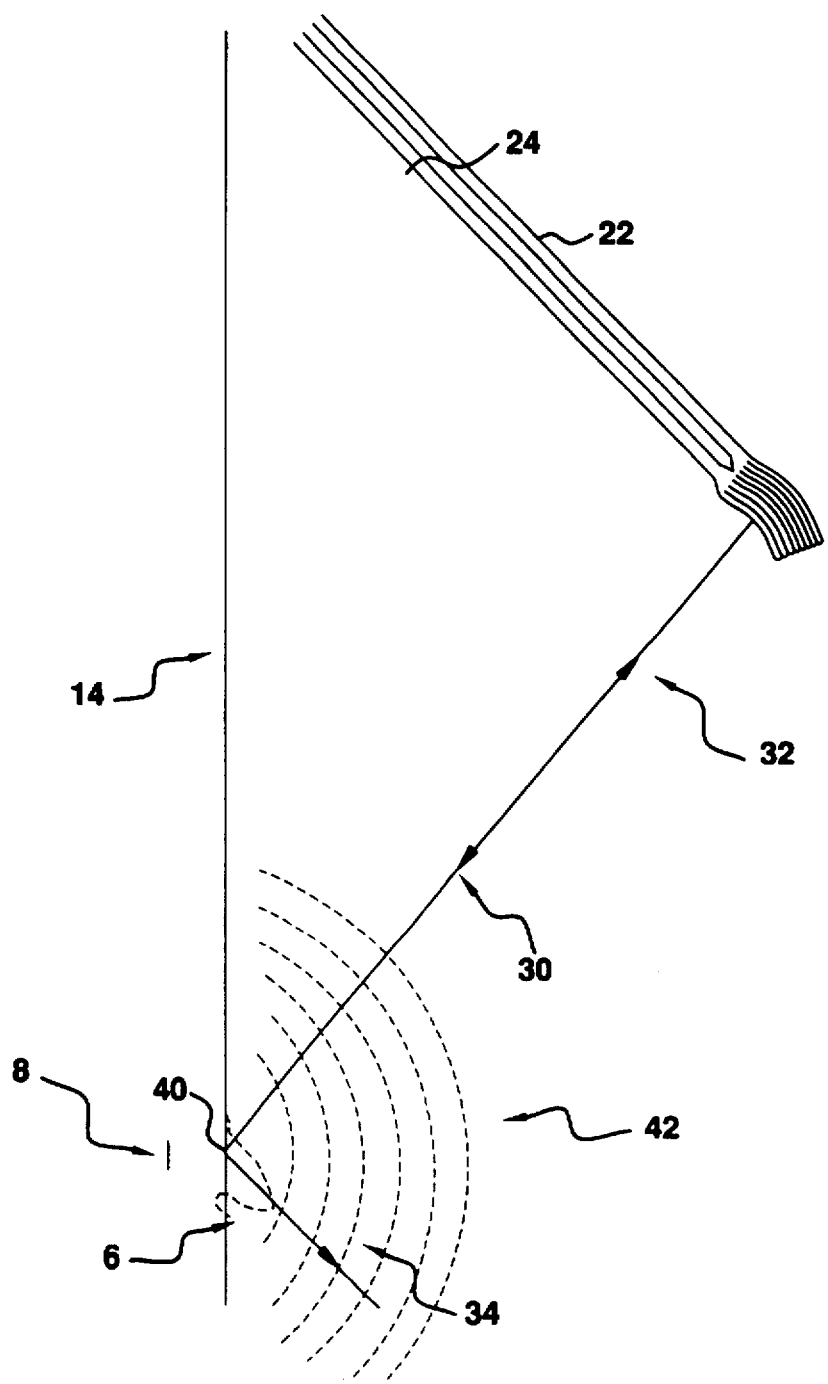
FIG. 3 is a view similar to FIG. 1 showing a second embodiment of the invention which can be used as an alternative to crossed EMATS; [and]

The alternate technique is illustrated in FIG. 3. Two collinear focused (or nonfocused) EMATs 22, 24 are rotated at a suitable angle with respect to the specular reflector. FIG. 3 shows the transmitted signal 30 and received signal 32 being sent and received by the EMATs 22, 24. FIG. 3 also shows the specular reflection 34 not detected by the EMAT receiver. In practice, the angle can be any convenient value (for example 45°) that provides good signal to noise ratio from the smallest expected flaw and eliminates the root and crown signal. The wavelength of sound will be sufficiently close to the dimensions of the point diffractors on the flaw, and thus the flaw acts as a point source 40 or series of point sources and exhibits a wide angular diffraction pattern 42.

The results are exactly analogous to those described for the crossed beam sensor. This technique has the advantage that the angle can be easily changed.

The invention eliminates the presence of the confusing crown and root signals. As a result, the data from the examination of the welds is much more easily examined. The simplicity in data interpretation resulting from the invention together with the elimination of couplant with EMATs greatly improves the automation of weld inspections. The use of this technique allows the position of the sensor to be much closer to the weld than with other techniques because the flaw signals are not obscured by the crown and root signals.

Both techniques detect flaws of any orientation. The only orientation that the sensor is not sensitive to is a case where a crack is parallel to the sound beam. This is solved by using two sensors, side by side, in a manner that the sound beams intersect each other in the weld. Therefore, if a crack is parallel to the sound beam from one sensor, it is detected by the other sensor. Diffraction with two sensors at an angle to each other with respect to the weld center line thus makes the detection of all flaw orientations possible. This capability has been demonstrated in practice for all flaw orientations in both aluminum and steel welds.

Figure 4:
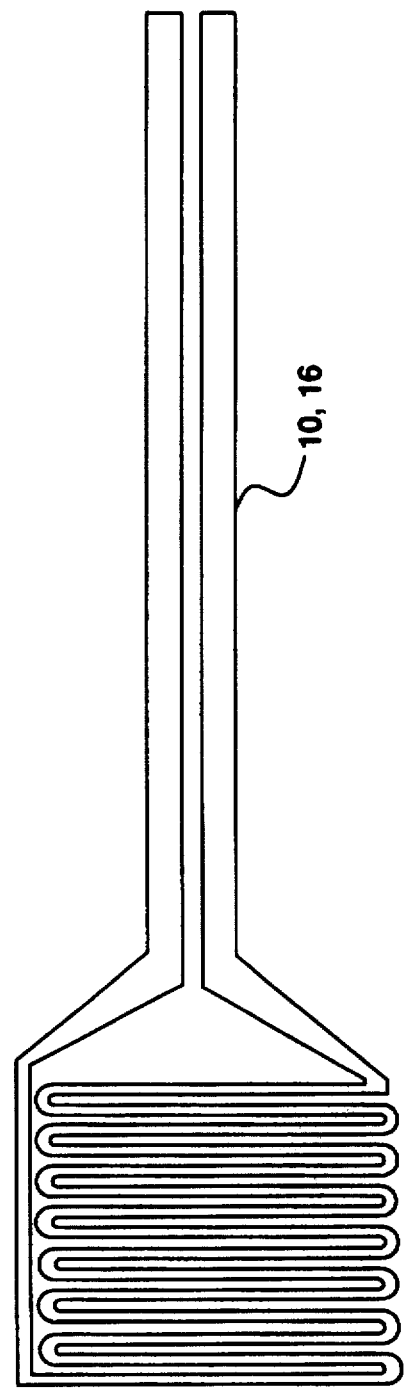
FIG. 4 is an enlarged view of the transducer which can be used either as a transmitting or receiving transducer, for the present invention.

FIG. 4 illustrates a typical EMAT, which can be used with the crossed sensor of the present invention, including dimensions. The EMAT of FIG. 4 is advantageously an SV, 2 MHz transducer.

The transmitter and receiver EMATs, both illustrated in FIG. 4, are mounted on 2 mil thick sheets of kapton, with the side of the kapton opposite the coils covered with 5 mil thick high molecular weight polyethylene. The side containing the coils was covered with a 1 mil thick sheet of polyethylene to serve as an electrical insulator. When the two coils are placed together in a "sandwich" configuration, one of the EMATs serves as transmitter and the other as a receiver.

Figure 5:
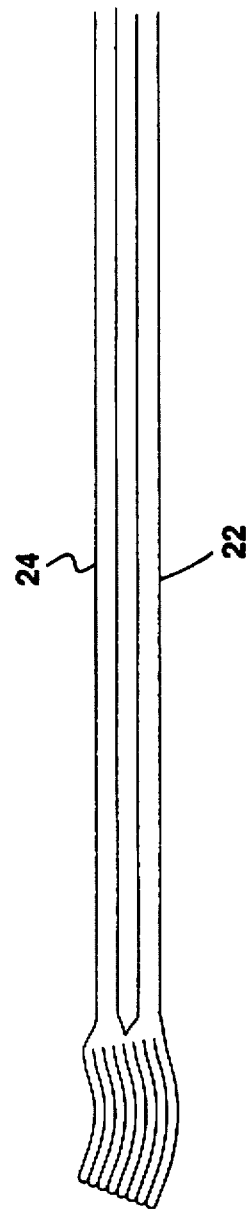
FIG. 5 is an enlarged view of the transducer as transmitting and receiving transducer for the alternate technique of the present invention showing dimensions in inches.
Figure 6:
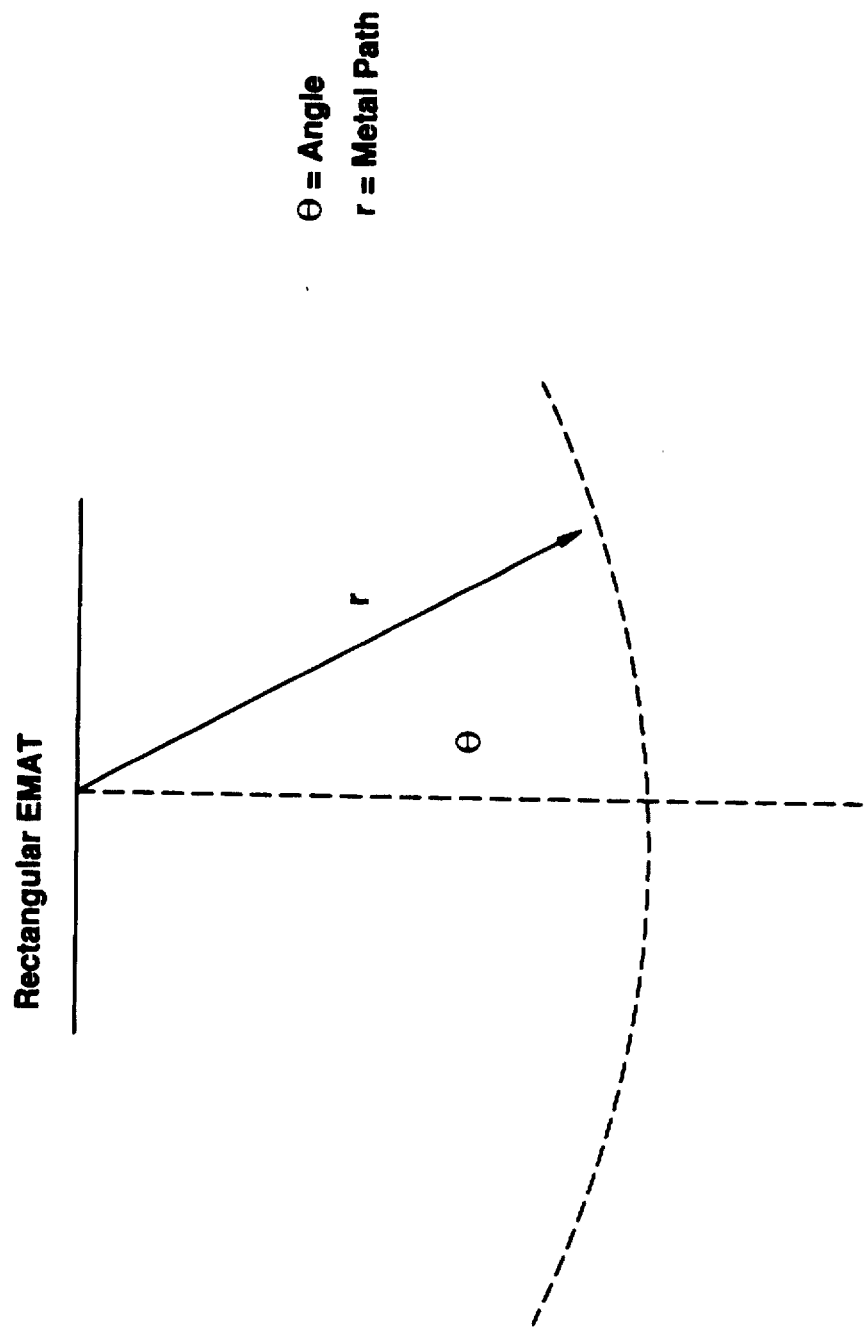
FIG. 6 shows the parameters that were used in plotting the theoretical curve for the diffraction pattern (or directivity pattern) of the transmitter EMAT curve.

FIG. 5 illustrates a typical collinear, focused sensor that can be used with the alternate technique. The pitch-catch EMAT in FIG. 5 is a two MHz SV shear wave sensor. The transmitter and receiver coils are mounted on 2 mil thick sheet of Kapton and covered with 5 mil thick high molecular weight polyethylene. The outer coil is typically the transmitter and the inner coil is typically the receiver.

The source of the magnetic field is two neodymium-iron-boron magnets. The two magnets were placed together with a thin copper sheet and thin sheet of cardboard taped to the bottom of the magnet to prevent sound propagating into the magnets themselves. The magnets were placed on the combination EMAT, and the transmitter was rotated at the desired angle with respect to the receiver to achieve the embodiment of FIG. 1.

While specific embodiments of the invention have been shown and described in detail to illustrate the application of the principles of the invention, it will be understood that the invention may be embodied otherwise without departing from such principles.

What is claimed is:

1. A method of inspecting for flaws in a specular reflector, the reflector being electrically conductive, the method comprising the steps of:

transmitting an acoustic beam with an electromagnetic acoustic transmitting transducer along a beam axis toward the specular reflector for producing a reflected acoustic beam, the transmitted acoustic beam having side lobes with zero points therebetween, at least some of the side lobes being major side lobes of a specular reflection produced by the transmitted beam from the specular reflector;

receiving the reflected beam using an electromagnetic acoustic receiving transducer at an angle to the beam axis, the angle being selected to be at one of the zero points and past all of the major lobes of the specular reflection of the transmitted acoustic beam; and detecting a flaw in the specular reflector based upon changes in the received acoustic beam.

2. A method according to claim 1, wherein the specular reflector comprises a conducting material containing a weld having a root and a crown which normally produce root and crown signals in the reflected beam, the method including transmitting the acoustic beam toward the weld and receiving the reflected acoustic beam which is substantially free of root and crown signal and, however, contains signals corresponding to a flaw in the weld.

3. A method according to claim 1, wherein the flaws include natural flaws.

4. A method according to claim 1, wherein each of the transmitting and receiving transducers have a transducer axis, the method including maintaining the transmitting transducer axis perpendicular to a surface of the specular reflector and maintaining the receiving transducer axis at the angle.

5. A method for inspecting flaws in a specular reflector, comprising the steps of:

transmitting an acoustic beam with an electromagnetic acoustic transmitter at an angle toward the specular reflector for producing a reflected acoustic beam, the transmitted acoustic beam having side lobes with zero points therebetween, at least some of the side lobes being major side lobes of a specular reflection produced by the transmitted acoustic beam from the specular reflector;

positioning an electromagnetic acoustic receiver in a collinear relationship with respect to the electromagnetic acoustic transmitter;

receiving the reflected beam using the electromagnetic acoustic receiver;

rotating the electromagnetic acoustic transmitter and receiver at the angle to the specular reflector, the angle being selected to be at one of the zero points and past all of the major side lobes of the specular reflection of the transmitted acoustic beam; and detecting a flaw in the specular reflector based upon changes in the received acoustic beam.

6. An apparatus for detecting flaws in a specular reflector, the reflector being electrically conductive, the apparatus comprising:

an acoustic transmitting transducer for directing a transmitted acoustic beam along a beam axis toward the specular reflector for producing a reflected acoustic beam, the transmitted beam having side lobes with zero points therebetween, at least some of the side lobes being major side lobes of a specular reflection produced by the transmitted acoustic beam from the specular reflector; and an electromagnetic acoustic receiving transducer for receiving the reflected beam, at an angle to the beam axis, the angle being selected to be at one of the zero points and past all of the major lobes of the specular reflection of the transmitted beam, wherein a flaw in the specular reflector is detected based upon changes in the received reflected beam.

7. An apparatus according to claim 6, wherein the transmitting and receiving transducers each have respective transducer axes which are at the angle with respect to each other.

8. An apparatus according to claim 6, wherein the flaws include natural flaws.

* * * * *